United States Patent
Newell-Price (10) Patent No.: US 9,216,221 B2
(45) Date of Patent: Dec. 22, 2015

(54) MEDICAMENT AND METHOD OF DIAGNOSIS FOR TREATING SUBCLINICAL CUSHING'S SYNDROME

(75) Inventor: John Newell-Price, Sheffield (GB)

(73) Assignee: University of Sheffield, Sheffield (GB)

( * ) Notice: Subject to any disclaimer, the term of this patent is extended or adjusted under 35 U.S.C. 154(b) by 889 days.

(21) Appl. No.: 13/128,225

(22) PCT Filed: Nov. 7, 2008

(86) PCT No.: PCT/GB2008/003751
§ 371 (c)(1), (2), (4) Date: May 6, 2011

(87) PCT Pub. No.: WO2010/052445
PCT Pub. Date: May 14, 2010

(65) Prior Publication Data
US 2011/0224179 A1    Sep. 15, 2011

(51) Int. Cl.
| | |
|---|---|
| A61K 31/495 | (2006.01) |
| A61K 45/06 | (2006.01) |
| A61K 31/10 | (2006.01) |
| A61K 31/165 | (2006.01) |
| A61K 31/18 | (2006.01) |
| A61K 31/357 | (2006.01) |
| A61K 31/40 | (2006.01) |
| A61K 31/415 | (2006.01) |
| A61K 31/4164 | (2006.01) |
| A61K 31/4196 | (2006.01) |

(Continued)

(52) U.S. Cl.
CPC .................. *A61K 45/06* (2013.01); *A61K 31/10* (2013.01); *A61K 31/165* (2013.01); *A61K 31/18* (2013.01); *A61K 31/357* (2013.01); *A61K 31/40* (2013.01); *A61K 31/415* (2013.01); *A61K 31/4164* (2013.01); *A61K 31/4196* (2013.01); *A61K 31/439* (2013.01); *A61K 31/44* (2013.01); *A61K 31/485* (2013.01); *A61K 31/496* (2013.01); *A61K 31/515* (2013.01); *A61K 31/5375* (2013.01); *A61K 31/56* (2013.01)

(58) Field of Classification Search
CPC .... A61K 31/495; A61K 31/4444; A61K 8/35
See application file for complete search history.

(56) References Cited

U.S. PATENT DOCUMENTS

| | | |
|---|---|---|
| 2002/0147336 A1 | 10/2002 | Dow et al. |
| 2004/0266831 A1 | 12/2004 | Robinson et al. |
| 2008/0206138 A1 | 8/2008 | Zolle et al. |

FOREIGN PATENT DOCUMENTS

| | | |
|---|---|---|
| EP | 1 886 695 A1 | 2/2008 |
| WO | WO 00/54766 | 9/2000 |

(Continued)

OTHER PUBLICATIONS

Fallo et al., "Response of hypertension to conventional antihypertensive treatment and/or steroidogenesis inhibitors in Cushing's syndrome," J Intern Med 234(6):595-598, 1993.*

(Continued)

*Primary Examiner* — Rosanne Kosson
(74) *Attorney, Agent, or Firm* — Klarquist Sparkman, LLP (57) ABSTRACT

We disclose a diagnostic test to determine suitable therapeutic intervention of subjects suffering from subclinical Cushing's syndrome [SCS] and also agents that antagonize the action of cortisol or inhibit excess cortisol production in the treatment of conditions such as SCS in the presence of an adrenal incidentaloma.

7 Claims, 3 Drawing Sheets

(51) Int. Cl.

| | | |
|---|---|---|
| A61K 31/439 | (2006.01) | |
| A61K 31/44 | (2006.01) | |
| A61K 31/485 | (2006.01) | |
| A61K 31/496 | (2006.01) | |
| A61K 31/515 | (2006.01) | |
| A61K 31/5375 | (2006.01) | |
| A61K 31/56 | (2006.01) | |

(56) References Cited

FOREIGN PATENT DOCUMENTS

| WO | WO 02/080930 A1 | 10/2002 |
|---|---|---|
| WO | WO 2005/087769 A1 | 9/2005 |
| WO | WO 2005/118557 A2 | 12/2005 |
| WO | WO 2005/118581 A1 | 12/2005 |
| WO | WO 2006/014394 A1 | 2/2006 |

OTHER PUBLICATIONS

Shalet et al., "Pharmacological treatment of hypercortisolism," Curr Opin Endocrinol Diabetes and Obesity 15(3):234-238, Jun. 2008.*

Benagiano et al., "Selective Progesterone Receptor Modulators 3: Use in Oncology Endocrinology and Psychiatry," *Expert Opinion on Pharmacotherapy* 9(14):2487-2496 (Oct. 1, 2008).

Höfle et al., "Adrenocortical Carcinoma Evolving after Diagnosis of Preclinical Cushing's Syndrome in an Adrenal Incidentaloma," *Hormone Research* 50:237-242 (Oct. 1, 1998).

International Search Report and Written Opinion from the parent PCT Application No. PCT/GB2008/003751, 21 pages (Jul. 31, 2009).

Mitchell et al., ""Subclinical Cushing's Syndrome" is not Subclinical: Improvement after Adrenalectomy in 9 Patients," *Surgery* 142(6):900-905 (Dec. 6, 2007).

Ohmori et al, "Preclinical Cushing's Disease Characterized by Massive Adrenal Hyperplasia and Hormonal Changes After Three Years of Metyrapone Therapy," *Endocrine Journal* 54(3):391-97 (Jun. 1, 2007).

Reincke, "Subclinical Cushing's Syndrome," *Endocrinology and Metabolism Clinics of America* 29(1):43-56 (Mar. 1, 2000).

Reznik et al., "Aberrant Adrenal Sensitivity to Multiple Ligands in Unilateral Indcidentaloma with Subclinical Autonomous Cortisol Hypersecretion: a Prospective Clinical Study," *Clinical Endocrinology* 61:311-319 (Sep. 2004).

* cited by examiner

MEDICAMENT AND METHOD OF DIAGNOSIS FOR TREATING SUBCLINICAL CUSHING'S SYNDROME

CROSS REFERENCE TO RELATED APPLICATIONS

This is the U.S. National Stage of PCT Application No. PCT/GB2008/003751, filed on Nov. 7, 2008, which was published in English under PCT Article 21(2).

BACKGROUND OF THE INVENTION

1. Field of the Invention

The invention relates to agents that inhibit the production of excess cortisol, or antagonize its effects, in the prevention or treatment of conditions such as subclinical Cushing's syndrome [SCS]; medicaments and pharmaceutical compositions comprising the agents, combinations of agents; and also to a diagnostic test to determine suitable therapeutic intervention of subjects suffering from SCS.

2. Description of Related Art

Cortisol, also called the "stress hormone", is secreted by the adrenal glands which are adjacent the kidneys. Cortisol secretion increases when the body is stressed, either physically or psychologically. Cortisol is released from the adrenal gland under the regulation of ACTH derived from the pituitary gland. There is a circadian rhythm to cortisol release with high levels first thing in the morning and very low levels around midnight. ACTH and thus cortisol levels begin to rise between 2-3 am and peak between 7-9 am gradually falling over the day to a nadir between 8 pm and 2 am. Disease conditions associated with excess cortisol secretion include Cushing's syndrome also referred to as hypercortisolism or hyperadrenocorticism and typically results from excess cortisol production due to a pituitary adenoma. Cushing's syndrome has a complex pathology and symptoms include weight gain, telangiectasia, skin thinning, bruising, insomnia, psychiatric disorders or depression, impaired cognition or memory, osteopenia or osteoporosis, obesity, persistent hypertension, insulin resistance which can lead to impaired fasting glucose or impaired glucose tolerance or diabetes mellitus, dyslipidemia, metabolic syndrome, coagulation disorders, proximal muscle weakness, hirsutism, amenorrhea. Untreated Cushing's disease can result in atherosclerosis, heart disease and increased mortality.

A related disease associated with excess cortisol production is subclinical Cushing's syndrome [SCS]. This condition is commonly associated with adrenal incidentaloma. Incidentaloma's are mostly benign non-secreting tumours discovered by imaging studies performed for unrelated reasons. In approximately 10 to 15% of cases, they produce supraphysiological amounts of cortisol. The levels are insufficient to cause clinical features typically associated with Cushing's syndrome. SCS is common in the general population (~1% or more of those >70 y in hospitalized or health-screened populations), and contributes to overall cardiovascular morbidity and mortality. A major problem is that management of SCS is not established. Approximately 90% of patients with SCS have hypertension; over 60% have impaired glucose tolerance or diabetes mellitus, obesity and osteoporosis or abnormal biochemical markers of bone turnover, 50% have dyslipidemia and abnormalities in hemostatic parameters. Carotid intima-media thickness is increased and atherosclerotic plaques are more frequent in patients than in controls.

In SCS there is the potential to permanently reduce these risks, and to improve bone health, by adrenalectomy. Only a very limited number of individuals with SCS are subjected to adrenalectomy. In those that have undergone this procedure improvements have been found in blood pressure (~10 mmHg drop in systolic BP), lipid profiles, fibrinogen levels, biochemical markers of bone turnover and glycaemic control. However, a problem is deciding whether adrenal surgery will be of benefit for a given patient with SCS, and the basis for selection for such permanent and invasive intervention is not established.

There is a need to provide a treatment regime for controlling SCS and a diagnostic test to determine an appropriate treatment regime for a subject suffering from SCS. The response of subjects to the administration of these agents will also allow an objective means to determine if a subject suffering from SCS would benefit from adrenalectomy.

Glucocorticoid receptor antagonists are known in the art. For example mifepristone (11-[4-(Dimethylamino)phenyl]-17-hydroxy-17-[1-propynyl]-[11β,17β]-estra-4,9-dien-3-one), a derivative of the synthetic progestin norethindrone, is a potent competitive glucocorticoid and progesterone receptor antagonist. Mifepristone is also known as RU486. Mifepristone causes glucocorticoid antagonism by reducing translocation of the receptor to the nucleus and also by antagonising glucocorticoid-dependent transcriptional activity. In man the administration of mifepristone at >200 mg/day blocks central and peripheral glucocorticoid action with resultant activation of the HPA axis. Selective, nonsteroidal glucocorticoid receptor antagonists have been derived from RU486 for instance as described by Morgan et al. (2002) in J. Med. Chem. 45, 2417-2424, as CP-394531, and CP-409069. A further example is RU43044 which is a selective glucocorticoid receptor antagonist. Other nonsteroidal glucocorticoid receptor antagonist compounds are described for example in following patents and patent applications: U.S. Pat. No. 6,380,223, U.S. Pat. No. 6,436,986, U.S. Pat. No. 6,468,975, US2002/0147336, US 2002/0107235, US2004/0014741, US2004/0176595, WO2004/009017, WO 2004/110385, WO2004/111015, US2004/0266758, US2004/0266831, WO2001/16128 WO2006/084917 and WO2008/017658 each of which is incorporated by reference.

An alternative means to oppose the actions of cortisol is to reduce circulating levels by blocking cortisol synthesis using inhibitors of adrenal steroidogenesis. Cortisol synthesis inhibitory properties have been ascribed to several drugs. For instance, ketoconazole, was initially developed as an antifungal therapy. The drug inhibits unselectively the synthesis corticosteroids and at higher doses the synthesis of testosterone. Recently, the use of ketoconazole in cardiovascular and metabolic diseases has been claimed by e.g. U.S. Pat. No. 6,274,582, U.S. Pat. No. 6,642,236. Further examples include aminogluthetimide and metyrapone. Aminogluthetimide blocks the conversion of cholesterol to pregnenolone by inhibiting desmolase which inhibits the synthesis of many steroids including cortisol. Metyrapone blocks cortisol synthesis by inhibition of steroid 11 beta hydroxylase. Other examples include trilostane, etomidate, epostane, thiopentone and ketotrilostane.

This disclosure relates to a diagnostic test to determine a suitable treatment regime for a subject suffering from excess cortisol production, for example subclinical Cushing's syndrome and also the treatment of the condition by administration of agents that inhibit the synthesis or activity of cortisol, or by surgical intervention.

SUMMARY

According to an aspect of the invention there is provided a diagnostic test, to determine a suitable treatment regime for a subject suffering from or having a pre-disposition to subclinical Cushing's syndrome or incidentaloma comprising:
  i) obtaining a biological sample from the subject; determining the level of cortisol in the subject and comparing this to control cortisol levels as a measure of subclinical Cushing's syndrome;
  ii) administering an effective amount of at least one agent to the subject to inhibit the synthesis or activity of cortisol in the subject; and
  iii) analysing the response of the subject to the administration of the agent to determine the improvement or not of the subject's condition.

In a preferred method of the invention, the diagnostic test aims at developing a clinical decision-making tool to inform the critical decision as to whether to proceed to adrenalectomy or not, or to use glucorticoid receptor antagonists and/or inhibitor of adrenal steroidogenesis.

In a preferred method of the invention, the diagnostic test aims at developing a clinical decision-making tool to inform if hypertension and/or, glucose metabolism impairment, glucose tolerance impairment, diabetes and/or osteoporosis are cortisol-dependent.

In a preferred method of the invention wherein there is an improvement in the subject's condition, the subject is either administered a unit dose of the agent in a controlled regime to maintain control of the subject's condition or to an alternative treatment regime; preferably said alternative treatment regime is surgical intervention, for example adrenalectomy.

In an alternative preferred method of the invention wherein the subject's condition does not improve a treatment regime is elected; preferably said alternative treatment regime is to avoid unnecessary surgical intervention, for example adrenalectomy; preferably said alternative treatment regime is to continue symptomatic treatment for hypertension and/or glucose metabolism impairment and/or osteoporosis.

In a preferred method of the invention wherein there is an improvement in the subject's condition, this means that the diagnosis test is positive; preferably this means that hypertension and/or glucose metabolism impairment and/or osteoporosis are linked to subclinical Cushing's syndrome or incidentaloma; preferably this means that hypertension and/or glucose tolerance impairment or diabetes and/or osteoporosis are linked to subclinical Cushing's syndrome or adrenal incidentaloma.

In an alternative preferred method of the invention wherein the subject's condition does not improve, this means that the diagnosis test is negative; preferably said this means that hypertension and/or glucose metabolism impairment and/or osteoporosis are not linked to subclinical Cushing's syndrome or adrenal incidentaloma; preferably said, this means that hypertension and/or glucose tolerance impairment or diabetes and/or osteoporosis are not linked to subclinical Cushing's syndrome or adrenal incidentaloma.

In a preferred method of the invention said agent is a glucocorticoid receptor antagonist.

DETAILED DESCRIPTION OF SEVERAL EMBODIMENTS

The term "glucocorticoid receptor antagonist" refers to any agent which partially or completely inhibits (i.e. antagonizes) the binding of a glucocorticoid receptor agonist, such as cortisol.

In a preferred method of the invention said glucocorticoid receptor antagonist is mifepristone.

The term "mifepristone" also referred to as RU486 or 17-beta-hydroxy-11-beta-(4-dimethyl-aminophenyl)-17-alpha-(1-propynyl)-estra-4,9-dien-3-one, refers to a molecule which belongs to a family of molecules sharing the same mechanism of action), including 11-beta-(4-dimethylaminophenyl)-17-beta-hydrox17-alpha-(I-propynyl)-estrn-4,9-dien-3-one), or analogues thereof, which bind to the glucocorticoid receptor, typically with high affinity, and inhibit the biological effects initiated/mediated by the binding of cortisol to a glucocorticoid receptor.

Figure 1:
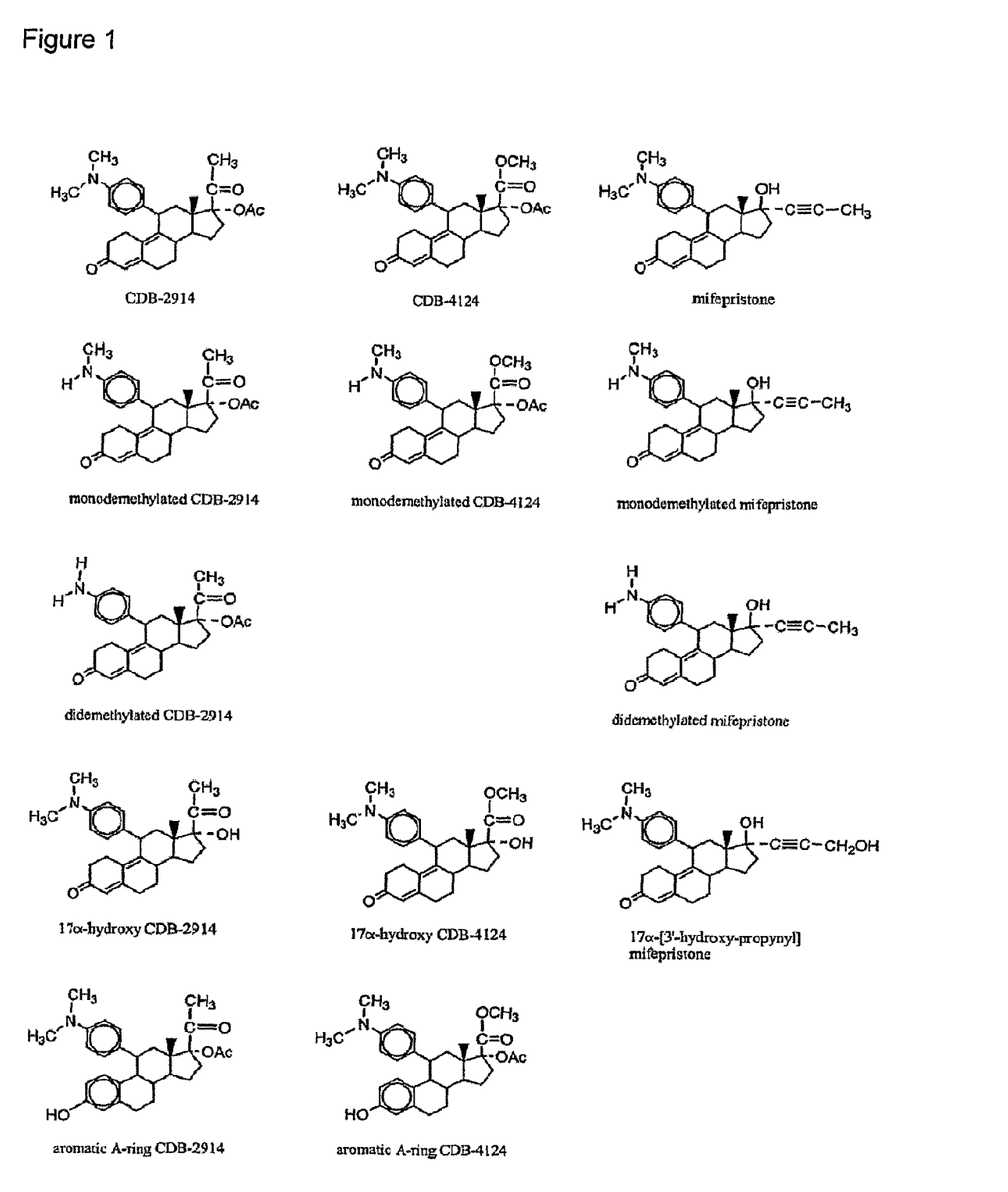
FIG. 1 illustrates non-limiting examples of glucocorticoid receptor antagonists.
Figure 2:
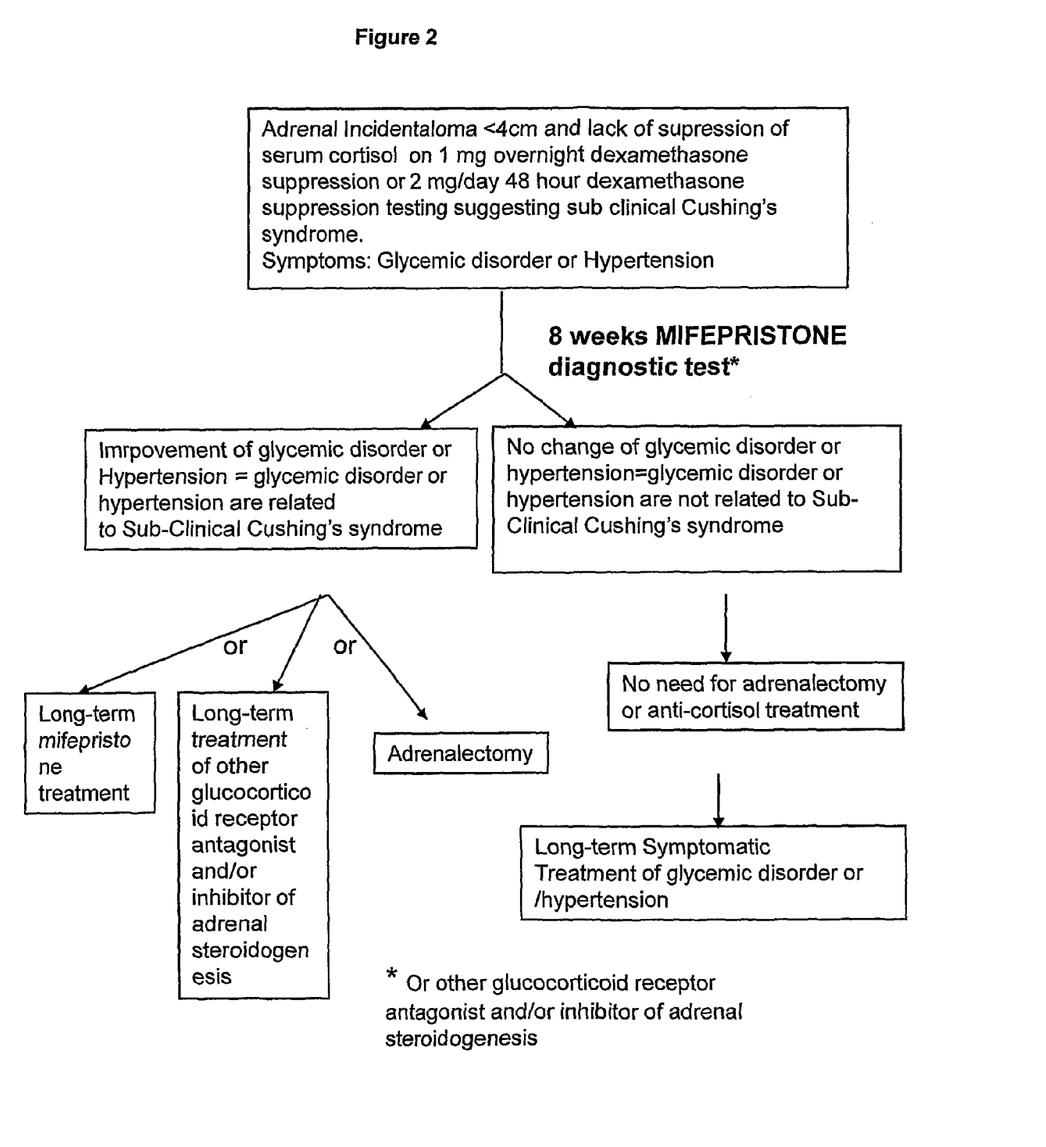
FIG. 2 illustrates a non-limiting embodiment of the treatment regime herein disclosed; Mifepristone test demonstrates if diabetes or hypertension are caused by sub-clinical Cushing's syndrome or not (are cortisol-dependent or not)
Figure 3:
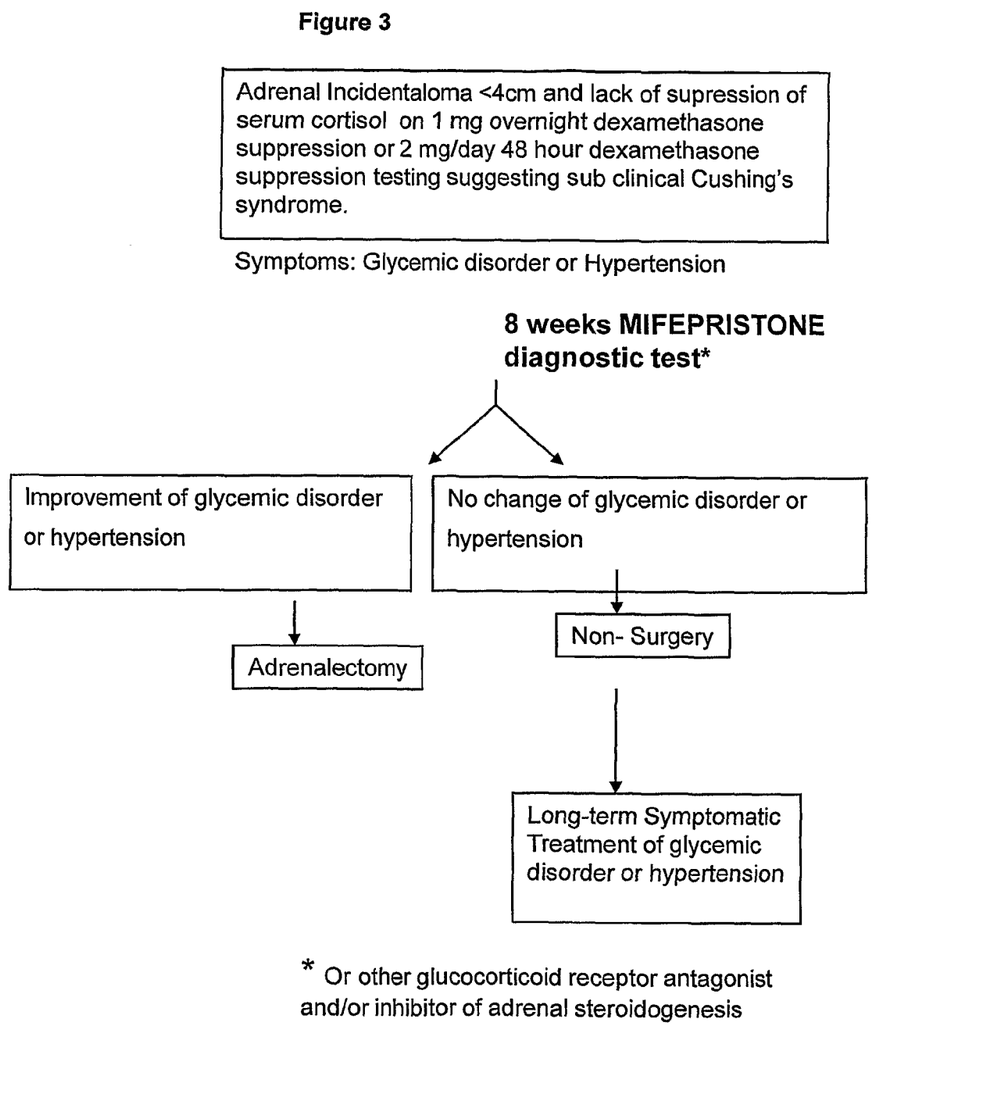
FIG. 3 illustrates a further embodiment of the treatment regime herein disclosed. Diagnostic Test for subclinical CS-incidentaloma This test will help to select which patient would benefit from adrenalectomy

In an alternative preferred method of the invention said glucocorticoid receptor antagonist is selected from the group illustrated in FIG. 1.

In a most preferred embodiment, the steroidal glucocorticoid receptor antagonist is mifepristone.

Examples of non-steroidal glucocorticoid receptor antagonists include, without limitation, N-(2-[4,4',441-trichlorotrityl]oxyethyl)morpholine; 1-(2[4,4',4"-trichlorotrityl]oxyethyl)-4-(2-hydroxyethyl)piperazine dimaleate; N-([4,4',4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl) benzhydrol; 5-(5-methoxy-2-(N-methylcarbamoyl)-phenyl) dibenzosuberol; N-(2-chlorotrityl)-L-prolinol acetate; 1-(2-chlorotrityl)-1,2,4-triazole; 1, S-bis(4,4',4"-trichlorotrityl)-1,2,4-triazole-3-thiol; 4.alpha.(S)-Benzyl-2(R)-chloroethynyl-1,2,3,4,4.alpha., 9,10,10.alpha. (R)-octahydrophenanthrene-2,7-diol ("CP 394531"), 4.alpha. (S)-Benzyl-2(R)-prop-1-ynyl-1,2,3,4,4.alpha., 9,10,10.alpha. (R)-octahydro-phenanthrene-2,7-diol ("CP-409069"), trans-(1R,2R)-3,4-dichloro-N-methyl-N-[2-1 pyrrolidinyl)cyclohexyl] benzeneacetamide, bremazocine, ethylketocyclazocine and naloxone.

In another embodiment, the non-steroidal glucocorticoid antagonist is one of the series synthesized by Corcept therapeutics. WO2006/014394, incorporated herein by reference, reports the synthesis and biological characterization of 48 novel 5,6-substituted pyrimidine-2,4-dione GR modulators. The most active compounds are compounds of formula I (I)

wherein
R1 is H and R2 is H or Cl,
or R1 is o-chloro or m-chloro and R2 is H.

In WO05/087769, incorporated herein by reference, Corcept therapeutics described the synthesis and biological testing of 150 compounds with a tetracyclic core ring structure that they term as azadecalins. Preferred azadecalin antagonists are compounds of formula II wherein
R1 is F and R2 is pyrrolidine,
or R1 is t-butyl and R2 is selected from the group consisting of H, a phenyl group, and —CH$_2$—O—CH$_3$ In a further alternative method of the invention said agent is an inhibitor of adrenal steroidogenesis.

In a preferred method of the invention said inhibitor of adrenal steroidogenesis is selected from the group consisting of: ketoconazole, metyrapone, aminoglutethimide, trilostane, etomidate, epostane, thiopentone and ketotrilistane.

In a preferred method of the invention said inhibitor of adrenal steroidogenesis is ketoconazole.

In a preferred method of the invention said inhibitor of adrenal steroidogenesis is metyrapone.

In a preferred method of the invention said agent is a combination of cortisol lowering agents; preferably a combination of a glucocorticoid receptor antagonist and an inhibitor of adrenal steroidogenesis.

According to an aspect of the invention there is provided an agent that inhibits the synthesis or activity of cortisol for use in the prevention or treatment of subclinical Cushing's syndrome.

In a preferred embodiment of the invention subclinical Cushing's syndrome is caused by an adrenal incidentaloma.

According to an aspect of the invention there is provided an agent that inhibits the synthesis or activity of cortisol for use in the prevention or treatment of incidentaloma.

In a preferred embodiment of the invention agent is a glucocorticoid receptor antagonist.

In a preferred embodiment of the invention said glucocorticoid receptor antagonist is mifepristone.

In an alternative preferred embodiment of the invention said glucocorticoid receptor antagonist is RU-43044, Org 34517, Org 34850, or Org 34116.

In a most preferred embodiment, the steroidal glucocorticoid receptor antagonist is mifepristone.

Examples of non-steroidal glucocorticoid receptor antagonists include, without limitation, N-(2-[4,4',441-trichlorotrityl]oxyethyl)morpholine; 1-(2[4,4',4"-trichlorotrityl]oxyethyl)-4-(2-hydroxyethyl)piperazine dimaleate; N-([4,4',4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl)benzhydrol; 5-(5-methoxy-2-(N-methylcarbamoyl)-phenyl)dibenzosuberol; N-(2-chlorotrityl)-L-prolinol acetate; 1-(2-chlorotrityl)-1,2,4-triazole; 1,S-bis(4,4',4"-trichlorotrityl)-1,2,4-triazole-3-thiol; 4.alpha.(S)-Benzyl-2(R)-chloroethynyl-1,2,3,4,4.alpha., 9,10,10.alpha. (R)-octahydrophenanthrene-2,7-diol ("CP 394531"), 4.alpha. (S)-Benzyl-2(R)-prop-1-ynyl-1,2,3,4,4.alpha., 9,10,10.alpha. (R)-octahydro-phenanthrene-2,7-diol ("CP-409069"), trans-(1R, 2R)-3,4-dichloro-N-methyl-N-[2-1 pyrrolidinyl)cyclohexyl]benzeneacetamide, bremazocine, ethylketocyclazocine and naloxone.

In another embodiment, the non-steroidal glucocorticoid antagonist is one of the series synthesized by Corcept therapeutics. WO2006/014394, incorporated herein by reference, reports the synthesis and biological characterization of 48 novel 5,6-substituted pyrimidine-2,4-dione GR modulators. The most active compounds are compounds of formula I wherein
R1 is H and R2 is H or Cl,
or R1 is o-chloro or m-chloro and R2 is H.

In WO05/087769, incorporated herein by reference, Corcept therapeutics described the synthesis and biological testing of 150 compounds with a tetracyclic core ring structure that they term as azadecalins. Preferred azadecalin antagonists are compounds of formula II wherein
R1 is F and R2 is pyrrolidine,
or R1 is t-butyl and R2 is selected from the group consisting of H, a phenyl group, and —CH$_2$—O—CH$_3$ In an alternative embodiment of the invention said agent is an inhibitor of adrenal steroidogenesis.

In a preferred embodiment of the invention said inhibitor of adrenal steroidogenesis is selected from the group consisting of: ketoconazole, metyrapone, aminoglutethimide, trilostane, etomidate, epostane, thiopentone and ketotrilostane.

In a preferred embodiment of the invention said agent is a combination of agents that inhibit the synthesis or activity of cortisol; preferably a combination of a glucocorticoid receptor antagonist and an inhibitor of adrenal steroidogenesis.

According to a further aspect of the invention there is provided a pharmaceutical composition comprising: a glucocorticoid receptor antagonist, an inhibitor of adrenal steroidogenesis and an excipient.

The compositions of the invention are administered in effective amounts. An "effective amount" is that amount of a composition that alone, or together with further doses, produces the desired response. For example, a dose of 100-300 mg mifepristone or more preferably 200 mg mifepristone twice daily is administered to provide partial blockade of glucocorticoid receptor activity. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In the case of treating SCS the desired response is the symptomatic treatment of the consequences of the disease. This may involve only the partial improvement of the symptomatic consequences of the disease, although more preferably, it involves complete improvement of the symptomatic consequences of the disease. This can be monitored by routine methods. More particularly improvements in SCS can be monitored by any one of the following indicia:

Blood pressure: The difference in blood pressure compared to baseline, in systolic and/or diastolic blood pressure (BP) (resting and ambulatory)

Glucose homeostasis: Homeostasis model assessment of insulin resistance (HOMA-IR), and the insulin Sensitivity Index (ISI) as calculated from oral glucose tolerance test: insulin and glucose at −15, 0, 30, 60 and 120 minutes, with oral glucose 75 g at time 0 (except for those on insulin therapy, whose investigation will be limited to basal and 120 minute plasma glucose) and 2-hour glucose tolerance during a 75 g oral glucose tolerance test.

Lipid profiling: The difference in fasting lipids post treatment.

DEXA scan with measurement of total and abdominal fat mass: The difference in total and abdominal fat mass post treatment compared to baseline.

Bone Markers: Excess cortisol will suppress serum osteocalcin, a marker of bone formation, and thus the effect of antagonism of glucocorticoids or lowering cortisol is an increase in this marker, and give insight as to the effect on bone health. The other bone turnover markers are bone alkaline phosphatase, C-telepopeptide I (CTX-I) and N-terminal propeptide of type 1 procollagen (P1NP) are expected to decrease.

Urine steroid profile: The difference in urinary steroid profile post treatment.

Quality of Life: The difference between in depression, quality of life and fatigue questionnaires.

The pharmaceutical compositions used in the foregoing methods preferably are suitable for oral administration and contain an effective amount of an agent according to the invention for producing the desired response in a unit of weight or volume suitable for administration to a patient. The response can, for example, be measured by determining decrease of disease symptoms.

The doses of the agent according to the invention administered to a subject can be chosen in accordance with different parameters, in particular in accordance with the mode of administration used and the state of the subject. Other factors include the desired period of treatment, subject's body mass index, ACTH or cortisol (in plasma, urine or salivary) levels. In the event that a response in a subject is insufficient at the initial doses applied, higher doses (or effectively higher doses by a different, more localized delivery route) may be employed to the extent that patient tolerance permits.

Other protocols for the administration of agents will be known to one of ordinary skill in the art, in which the dose amount, schedule and mode of administration and the like vary from the foregoing. The administration of compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the agents of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulphuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. The compositions also may contain, optionally, suitable preservatives, such as: benzalkonium chloride; chlorobutanol; parabens and thimerosal. The agents of the invention can exist in different forms, such as acids, esters, salts and tautomers, for example, and the invention includes all variant forms of the agents.

Compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" in this context denotes an organic or inorganic ingredient, natural or synthetic, with which the active ingredient is combined to facilitate the application, [e.g. liposome based]. The components of the pharmaceutical compositions also are capable of being co-mingled with the molecules of the present invention, and with each other, in a manner such that there is no interaction which would substantially impair the desired pharmaceutical efficacy.

The compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion or as a gel. Compositions may be administered as aerosols and inhaled.

Compositions suitable for parenteral administration conveniently comprise a sterile aqueous or non-aqueous preparation of agent which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

According to a further aspect of the invention there is provided a method of treating subclinical Cushing's syndrome comprising administering an effective amount of at least one agent that inhibits the synthesis or activity of cortisol.

According to a further aspect of the invention there is provided a method of treating subclinical Cushing's syndrome comprising administering an effective amount of a glucocorticoid receptor antagonist and an inhibitor of adrenal steroidogenesis.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the figures, materials and methods:

EXAMPLES

Methodology
Determination of Cortisol Excess

Three main tests are used to demonstrate excess cortisol secretion: urinary free cortisol, dexamethasone suppression tests, and midnight plasma or salivary cortisol. In SCS urinary free cortisol is usually within the normal range, as this is a relatively insensitive marker of hypercortisolaemia, whilst a post-dexamethasone serum value of >60 nM (>1.9 ug/dl) in patients with adrenal incidentalomas is associated with excess hypertension, as is an elevated midnight cortisol sample. Plasma ACTH levels are usually in the lower end of the normal range, reflecting low-grade partial hypothalamo-pituitary-adrenal axis suppression, as a consequence of the low-grade excess autonomous secretion of cortisol from the adrenal.

In addition to these tests urinary steroid metabolite analysis by gas chromatography/mass spectrometry (GC/MS) is an invaluable tool allowing detailed analysis of the complete steroid output of an individual and, importantly, by analyzing substrate/product ratios, it facilitates the calculation of measures of steroidogenic enzyme activity. Decreased 5-alpha-reductase activity is a specific feature of Cushing's syndrome and distinguishes it from the polycystic ovary syndrome that is associated with increased 5alpha-reductase activity, though clinically both conditions may present with features of the metabolic syndrome (obesity, hypertension, impaired glucose tolerance). In addition urinary steroid GC/MS analysis allows the identification of decreased 11-beta-HSD2 activity in severe overt Cushing's syndrome due to the ectopic ACTH syndrome, a feature that is not apparent in SCS. GC/MS analysis will allow for a more detailed picture on the nature of glucocorticoid excess in adrenal incidentaloma than urinary free cortisol excretion alone.

Design

The period of study is 8 weeks. The first 4 intervention visits are weekly, and the next two 2-weekly. The overall study design and assessments is shown in Table 1, including assessments made for secondary endpoints: Intervention—Mifepristone 200 mg BD from week 0

Inclusion Criteria

Patients are eligible for inclusion if: they are over 18; have an adrenal incidentaloma with benign characteristics as assessed on CT or MRI; lack clinical features classically associated with Cushing's syndrome; have evidence of excess cortisol as shown by lack of suppression of serum cortisol on 1 mg over-night dexamethasone suppression or 2 mg/day 48 hour low-dose dexamethasone suppression testing; stable antihypertensive and diabetic medication for two months prior to study entry.

Exclusion Criteria

These include: evidence of local or systemic malignancy; overt Cushing's syndrome; severe uncontrolled diabetes mellitus or hypertension; Clinically significantly impaired cardiovascular function (e.g. stage IV cardiac failure); severe liver disease (liver enzymes≥3×the institutional upper limit of normal range); significantly impaired renal function (eGFR<30/min); uncontrolled severe active infection; treatment with approved or experimental steroidogenesis inhibitors, adrenolytic agents, within four weeks of admission; In women, known endometrial cancer, history of endometrial hyperplasia or vaginal bleeding of unknown cause; requirement for inhaled or systemic glucocorticoids for existing disease; impaired mental capacity or markedly abnormal psychiatric evaluation that precludes informed consent.

Treatment Regime

The dose of 200 mg twice daily is administered to provide blockade of glucocorticoid receptor activity. The interval is twice daily based on the known half-life of the drug and the wish to completely block glucocorticoid activity over the 24-hour period, with reduced risk of overt glucocorticoid deficiency, and to minimize the possibility of a rebound effect of increased cortisol exposure at the end of the dose interval, as may happen by using a single dose of mifepristone 400 mg/24 hours.

Safety

Clinical assessment by BP, P, temperature, weight and questioning for fatigue, headache, anorexia, nausea, arthralgia, myalgia, and abdominal pain (potential glucocorticoid deficiency, a predictable effect of mifepristone based on its known action) is made at each study visit. Clinical experience is, however, that even total adrenal insufficiency is well tolerated in the absence of physical or infective stressors. For safety purposes each patient is issued with a steroid card and with a supply of two dexamethasone 1 mg tablets (sufficient to overcome the effects of mifepristone 400 mg by taking dexamethasone 1 mg/day for 2 days) to be taken on the advice of the investigators if significant symptoms are reported. In such circumstances any study subject attends the Clinical Research Facility (CRF) either that day or the next working day, and data entered into the CRF accordingly, and the subject withdrawn. Other uncommon but documented side effects of mifepristone used at this dose and for this time period include: nausea, anorexia, asthenia, skin rash (maculopapular), increased eosinophil count, joint pain, hypokalaemia. When used for >3-6 months duration endometrial hyperplasia, vaginal bleeding, metrorragia and amenorrhea are described.

Statistical Analysis

This protocol follows an open-label, non-randomised design. All statistical analyses are performed with descriptive and exploratory purposes and the results of statistical tests with confidence interval, when given is considered an aid to evaluate the reliability of the observed result. The data is summarised with respect to demographic and baseline characteristics, efficacy, observation and measurements, safety observations and measurements.

The primary outcome analysed is change in the resting and 24-hour ambulatory blood pressure, and the 2-hour glucose on OGTT. Secondary endpoints are analysed in a similar fashion.

Outcome Measures

Primary end points are the difference at 8 weeks, compared to baseline, in systolic blood pressure (BP) (resting and ambulatory) and 2-hour glucose tolerance during a 75 g oral glucose tolerance test. BP is measured in the sitting position, left arm taken twice, separated by 5 mins, after 10 mins resting (according to British Hypertension Society, UK [BHS] guidelines). 24-hour ambulatory blood pressure will be measured using standard BHS-approved monitors.

The primary endpoints have been chosen, as they are associated with important clinical outcomes. Baseline 24 hour ambulatory BP monitoring will be performed between the first visit and randomisation (4 week interval) and again at weeks 4 and 8. The daytime and nocturnal BP as determined by 24-hour ambulatory monitoring will be assessed independently and together to take account of the influence of the circadian rhythm in serum cortisol Secondary end points are: compared to baseline: 1) the difference in BP and Glucose tolerance at 4 weeks; 2) homeostasis model assessment of insulin resistance (HOMA-IR), and the insulin Sensitivity Index (ISI) at 4 and 8 weeks, as calculated from oral glucose tolerance test: insulin and glucose at −15, 0, 30, 60 and 120 minutes, with oral glucose 75 g at time 0 (except for those on insulin therapy, whose investigation will be limited to basal and 120 minute plasma glucose); 3) the difference in the mean plasma 0900 h plasma ACTH, and salivary 0900 and 2400 h cortisol values at 4 and 8 weeks; 4) the difference in fasting lipids fasting lipids at 8 weeks; 5) the difference in bone turnover markers at 8 weeks; 6) difference in urinary steroid profile at week 8; 7) the difference between in depression, quality of life and fatigue questionnaires at 4 and 8 weeks. Tertiary endpoint will be any major cardiovascular adverse events at 8 weeks. Other biochemical safety parameters are summarized in the table above.

The level of morning plasma ACTH and salivary nocturnal cortisol increases under the action of the study drug and give a biological marker for the effect of blockade. The repeated measurement will give greater confidence in the observation of drug activity. Salivary cortisol is stable at room temperature and thus is collected by patients at home and brought or sent to the CRF. Similarly, assessment of the urinary steroid profile is determined to assess the effects of mifepristone and the influence of increased circulating ACTH. Excess cortisol will suppress serum osteocalcin, a marker of bone formation, and thus the predicted effect of mifepristone would be an increase in this marker, and give insight as to the effect on bone health.

Clinically overt Cushing's syndrome is associated with impairments in health-related subjective health status that does not fully return to normal for many years after treatment. In SCS it is not established if quality of life is impaired. In view of this and the potential effects of altering excess cortisol on mood and general well-being, three validated questionnaires are used to assess the effects of mifepristone therapy on health-related subjective health status. In addition to assessing any changes induced by mifepristone therapy the scores are compared to sex and age—matched controls drawn from questionnaire-specific reference cohorts (available at the University of Sheffield), to establish if these parameters are impaired in SCS.

Intervention

Treatment is in the form of an oral tablet of oral mifepristone twice-daily 200 mg (0900 h and 2100 h) for eight weeks. Patients attend the CRF at 0900 h fasted at weekly intervals from weeks 0-4, and then again at weeks 6 and 8. A major advantage to this study design, compared to performing adrenalectomy, is that the treatment is immediately reversible, is not associated with the inherent risks of surgery, and it will inform design of a larger study, and then whether an invasive approach by adrenal surgery is justified for study in this common patient group.

Instruments

A). Depression is measured by Beck Depression Inventory® (BDI®-II). The BDI-II takes approximately 10 minutes to complete. Each item has one numerical answer ranging from 0 (low depression) to 3 (maximum depression). Thus the total score ranges from 0 to 63.

B). Quality of life is measured by the Short Form (SF-36), a 36-item health survey questionnaire to record general well-being during the previous 30 days and overall evaluation of health. Scores are expressed on a 0-100 scale, and higher scores are associated with a better quality of life.

C). Fatigue is measured by Multidimensional Fatigue Index (MFI-20). This is a 5-point scale that comprises 20 statements to assess fatigue. Scores vary from 0-20, a high score indicating higher experienced fatigue.

TABLE 1

| | Week | | | | | | | |
|---|---|---|---|---|---|---|---|---|
| | -4 | 0 | 1 | 2 | 3 | 4 | 6 | 8 |
| | | | | Visit | | | | |
| | 1 | 2 | 3 | 4 | 5 | 6 | 7 | 8 |
| Informed Consent | ✓ | | | | | | | |
| Resting BP and clinical assessment | ✓ | ✓ | ✓ | ✓ | ✓ | ✓ | ✓ | ✓ |
| 24-hour BP (during week of study) | ✓ | | | | | ✓ | | ✓ |
| OGTT - 0, 15, 30, 60, 90, 120 mins samples for insulin and glucose | | ✓ | | | | ✓ | | ✓ |
| U + E | ✓ | ✓ | ✓ | ✓ | ✓ | ✓ | ✓ | ✓ |
| LFT | ✓ | | | | | | | ✓ |
| TSH | ✓ | | | | | | | ✓ |
| FBC | ✓ | ✓ | | | | ✓ | | ✓ |
| Fasting lipids | | ✓ | | | | | | ✓ |
| 0900h/2400h salivary cortisol | ✓ | ✓ | ✓ | ✓ | ✓ | ✓ | ✓ | ✓ |
| 0900h serum cortisol | | ✓ | ✓ | ✓ | ✓ | ✓ | ✓ | ✓ |
| Plasma ACTH | | ✓ | ✓ | ✓ | ✓ | ✓ | ✓ | ✓ |
| Bone turnover markers - formation, serum osteocalcin; resorption, urine NTX | ✓ | | | | | | | ✓ |
| Urinary steroid profile (during week of study) | ✓ | | | | | | | ✓ |
| Health-related quality of life questionnaires | ✓ | | | | | ✓ | | ✓ |

The invention claimed is:

1. A method to determine a suitable treatment regime for a subject suffering from or having a pre-disposition to subclinical Cushing's syndrome or adrenal incidentaloma, said method comprising:
  i) determining the level of cortisol in a sample from the subject and comparing said level to normal cortisol levels as a measure of subclinical Cushing's syndrome in the subject;
  ii) administering to the subject an effective amount of at least one agent that inhibits the synthesis or activity of cortisol; and
  iii) analyzing the improvement of hypertension and/or glucose metabolism and/or osteoporosis in said subject as a measure of the response of the subject to the administration of the agent, to determine an improvement or not of the subject's condition and define a suitable treatment regime;
  iv) detecting an improvement in hypertension and/or glucose metabolism and/or osteoporosis in the subject; and
  v) treating the subject by surgical intervention.

2. A method to determine a suitable treatment regime for a subject suffering from or having a pre-disposition to subclinical Cushing's syndrome or adrenal incidentaloma, said method comprising:
  i) determining the level of cortisol in a sample from the subject and comparing said level to normal cortisol levels as a measure of subclinical Cushing's syndrome in the subject;
  ii) administering to the subject an effective amount of at least one agent that inhibits the synthesis or activity of cortisol; and
  iii) analyzing the improvement of hypertension and/or glucose metabolism and/or osteoporosis in said subject as a measure of the response of the subject to the administration of the agent, to determine an improvement or not of the subject's condition and define a suitable treatment regime;
  iv) detecting no improvement in hypertension and/or glucose metabolism and/or osteoporosis in the subject; and
  v) treating the subject with a treatment regimen comprising symptomatic treatment for hypertension and/or glucose metabolism impairment and/or osteoporosis.

3. The method according to claim 1 wherein said surgical intervention is adrenalectomy.

4. The method according to claim 1 wherein said agent is an inhibitor of adrenal steroidogenesis.

5. The method according to claim 4 wherein said inhibitor of adrenal steroidogenesis is selected from the group consisting of: ketoconazole, metyrapone, aminoglutethimide, trilostane, etomidate, epostane, thiopentone and ketotrilostane.

6. The method according to claim 5 wherein said inhibitor of adrenal steroidogenesis is ketoconazole.

7. The method according to claim 5 wherein said inhibitor of adrenal steroidogenesis is metyrapone.

* * * * *